(12) United States Patent
Shao et al.

(10) Patent No.: US 10,973,464 B2
(45) Date of Patent: Apr. 13, 2021

(54) DEVICE AND METHOD FOR REMOVING ARTIFACTS IN PHYSIOLOGICAL MEASUREMENTS

(71) Applicants: Shiyun Shao, Singapore (SG); Kittipong Kasamsook, Singapore (SG)

(72) Inventors: Shiyun Shao, Singapore (SG); Kittipong Kasamsook, Singapore (SG)

(73) Assignee: NITTO DENKO CORPORATION, Osaka (JP)

( * ) Notice: Subject to any disclaimer, the term of this patent is extended or adjusted under 35 U.S.C. 154(b) by 1096 days.

(21) Appl. No.: 15/318,205

(22) PCT Filed: Jun. 13, 2014

(86) PCT No.: PCT/SG2014/000279
§ 371 (c)(1),
(2) Date: Dec. 12, 2016

(87) PCT Pub. No.: WO2015/190994
PCT Pub. Date: Dec. 17, 2015

(65) Prior Publication Data
US 2017/0128019 A1 May 11, 2017

(51) Int. Cl.
*A61B 5/00* (2006.01)
*G16B 40/00* (2019.01)
*A61B 5/024* (2006.01)
*A61B 5/02* (2006.01)

(52) U.S. Cl.
CPC ............ *A61B 5/721* (2013.01); *A61B 5/0015* (2013.01); *A61B 5/02416* (2013.01); *A61B 5/681* (2013.01); *A61B 5/725* (2013.01); *A61B 5/7207* (2013.01); *A61B 5/742* (2013.01); *G16B 40/00* (2019.02); *A61B 5/0022* (2013.01); *A61B 5/02* (2013.01); *A61B 5/6824* (2013.01); *A61B 2562/0219* (2013.01)

(58) Field of Classification Search
None
See application file for complete search history.

(56) References Cited

U.S. PATENT DOCUMENTS 5,513,649 A 5/1996 Gevins
7,920,919 B1 * 4/2011 Nabutovsky ....... A61B 5/04525
607/19

(Continued)

OTHER PUBLICATIONS

Peter Gibbs, "Reducing Motion Artifact in Wearable Bio-Sensors Using MEMS Accelerometers for Active Noise Cancellation," 2005 American Control Conference, Jun. 8-10, 2015, Portland, Oregon (6 pages).

(Continued)

*Primary Examiner* — Joanne M Hoffman
(74) *Attorney, Agent, or Firm* — Abelman, Frayne & Schwab (57) ABSTRACT

Device and method for removing artifacts in physiological measurements. The method can comprise the steps of obtaining a physiological signal of a user; obtaining corresponding motion data representative of motion of the user; determining whether the physiological signal is distorted; and if the physiological signal is determined to be distorted, identifying a noise reference and filtering the physiological signal with the noise reference.

22 Claims, 9 Drawing Sheets

(56) References Cited

U.S. PATENT DOCUMENTS

| | | | | |
|---|---|---|---|---|
| 2004/0111219 | A1* | 6/2004 | Gulati | B82Y 5/00 |
| | | | | 702/19 |
| 2011/0257554 | A1* | 10/2011 | Banet | A61B 5/0816 |
| | | | | 600/536 |
| 2012/0310052 | A1* | 12/2012 | Mahapatra | A61B 5/04017 |
| | | | | 600/301 |
| 2013/0197328 | A1* | 8/2013 | Diab | A61B 5/7214 |
| | | | | 600/324 |
| 2013/0211271 | A1* | 8/2013 | Kang | A61B 5/721 |
| | | | | 600/509 |
| 2013/0296666 | A1* | 11/2013 | Kumar | G01N 21/3151 |
| | | | | 600/310 |
| 2015/0208931 | A1* | 7/2015 | Kasamsook | A61B 5/02416 |
| | | | | 600/479 |
| 2016/0065840 | A1* | 3/2016 | Kim | G06F 1/1694 |
| | | | | 348/223.1 |
| 2017/0347948 | A1* | 12/2017 | Thein | A61B 5/4812 |

OTHER PUBLICATIONS

Meltem Izzetoglu, "Motion Artifact Cancellation in NIR Spectroscopy Using Wiener Filtering," IEEE Transactions on Biomedical Engineering, May 2005, vol. 52, No. 5, p. 934-38 (5 pages).

Office action from corresponding Japanese Patent Application No. 2016-572641, dated May 30, 2018 (9 pages, including English translation).

\* cited by examiner

ACC signal along y-axis (702) has the maximal amplitude and it is determined as the noise reference.

DEVICE AND METHOD FOR REMOVING ARTIFACTS IN PHYSIOLOGICAL MEASUREMENTS

CROSS-REFERENCE TO RELATED APPLICATIONS

This application is a National Phase of PCT/SG2014/000279, filed 13 Jun. 2014, the disclosure of which is incorporated herein by reference.

FIELD OF INVENTION

The present invention relates broadly to device and method for removing artifacts in physiological measurements.

BACKGROUND

Physiological sensors are generally highly sensitive to motion artifacts. An example of such sensors is a photoplethysmography (PPG) sensor. A PPG sensor relies on the light emitting diodes and photo detectors to produce a PPG signal that can be used to monitor various parameters, such as heart rate and oxygen saturation level in blood. Therefore, it would not be desirable that the measurement unit utilizes a PPG signal that is corrupted by motion artifacts.

One way to detect motion artifacts in a PPG signal from a device is to incorporate an accelerometer (ACC) sensor, preferably a tri-axial ACC, to detect whether motion is present. With the tri-axial ACC sensor, the device can sense more specifically how the motion is along each axis and thus, the output of the ACC sensor can be used as a reference indicative of motion artifacts in the PPG signal and to correct the PPG signal accordingly.

Adaptive filtering with motion signals captured by ACC provides a promising method for the removal of artifacts from PPG data distorted by motion. However, there are cases when the ACC signals are not correlated with the PPG distortion, and in such cases the signal quality of the PPG will deteriorate after filtering with the ACC signal as noise reference.

Furthermore, existing methods either combine the ACC signals along all the three axes or simply specify the ACC signal along a particular axis as the noise reference. However, under different motions, the motion artifacts in the PPG may be correlated with ACC signals along a different axis. In other words, either by using the ACC signals along a specified axis only or by combining the tri-axial ACC signals, it may not be possible to obtain a noise reference that is always well correlated with artifacts in PPG under different motions, thus lowering the performance of the adaptive filtering approach.

Embodiments of the present invention provide a system and method for removing artifacts in physiological measurements that seek to address at least one of the above problems.

SUMMARY

In accordance with a first aspect of the present invention there is provided a method for removing artifacts in physiological measurements, the method comprising the steps of obtaining a physiological signal of a user; obtaining corresponding motion data representative of motion of the user; determining whether the physiological signal is distorted; and if the physiological signal is determined to be distorted, identifying a noise reference and filtering the physiological signal with the noise reference.

Preferably, the method further comprises checking the reliability of the filtered physiological signal.

In accordance with a second aspect of the present invention there is provided a device for removing artifacts in physiological measurements, the device comprising a first sensor for obtaining a physiological signal of a user; a second sensor for obtaining corresponding motion data representative of motion of the user; and a processor configured for determining whether the physiological signal is distorted and, if the physiological signal is determined to be distorted, identifying a noise reference and for filtering the physiological signal with the noise reference.

Preferably, the processor is further configured for checking the reliability of the filtered physiological signal.

BRIEF DESCRIPTION OF THE DRAWINGS

Embodiments of the invention will be better understood and readily apparent to one of ordinary skill in the art from the following written description, by way of example only, and in conjunction with the drawings, in which.

DETAILED DESCRIPTION

Embodiments of the present invention provide a method and system for identifying a noise reference that is preferably well correlated with motion artifacts in PPG under different motions, from tri-axial ACC signals for adaptive filtering In other words, embodiments of the present invention can provide a method for eliminating undesired artifacts in physiological measurements due to body motions. Specifically, an embodiment of the invention relates to a method for the removal of motion artifacts from PPG signals from wearable sensors with an integrated tri-axial ACC. The PPG signals are subjected to a PPG distortion checking module, which checks whether PPG is motion distorted. If yes, the motion signal(s) captured by ACC that is/are correlated with motion artifacts in PPG will be identified and used as a noise reference for adaptive cancellation of motion artifacts in the physiological measurement. Then, a signal quality checking module judges the reliability of the filtered PPG. PPG recordings which are still distorted will be rejected so as to preferably ensure estimation of physiological parameters, e.g. heart rate. Such an embodiment of the present invention is advantageously able to achieve optimal or near optimal performance while being computationally inexpensive.

The present specification also discloses an apparatus, which may be internal and/or external to the wearable device in example embodiments, for performing the operations of the methods. Such apparatus may be specially constructed for the required purposes, or may comprise a general purpose computer or other device selectively activated or reconfigured by a computer program stored in the computer. The algorithms and displays presented herein are not inherently related to any particular computer or other apparatus. Various general purpose machines may be used with programs in accordance with the teachings herein. Alternatively, the construction of more specialized apparatus to perform the required method steps may be appropriate. The structure of a conventional general purpose computer will appear from the description below. In addition, the present specification also implicitly discloses a computer program, in that it would be apparent to the person skilled in the art that the individual steps of the method described herein may be put into effect by computer code. The computer program is not intended to be limited to any particular programming language and implementation thereof. It will be appreciated that a variety of programming languages and coding thereof may be used to implement the teachings of the disclosure contained herein. Moreover, the computer program is not intended to be limited to any particular control flow. There are many other variants of the computer program, which can use different control flows without departing from the spirit or scope of the invention.

Furthermore, one or more of the steps of the computer program may be performed in parallel rather than sequentially. Such a computer program may be stored on any computer readable medium. The computer readable medium may include storage devices such as magnetic or optical disks, memory chips, or other storage devices suitable for interfacing with a general purpose computer. The computer readable medium may also include a hard-wired medium such as exemplified in the Internet system, or wireless medium such as exemplified in the GSM mobile telephone system. The computer program when loaded and executed on such a general-purpose computer effectively results in an apparatus that implements the steps of the preferred method.

The invention may also be implemented as hardware modules. More particularly, in the hardware sense, a module is a functional hardware unit designed for use with other components or modules. For example, a module may be implemented using discrete electronic components, or it can form a portion of an entire electronic circuit such as an Application Specific Integrated Circuit (ASIC). Numerous other possibilities exist. Those skilled in the art will appreciate that the system can also be implemented as a combination of hardware and software modules.

The described embodiments of the invention described herein relate to a wearable device and a method for removing motion artifact from a physiological signal, based on an ACC signal, acquired from the user.

In one embodiment, the device can be worn on any location of the user with sufficient skin area to allow the light emitting diode-photo detector (LED-PD) arrangement to acquire the PPG signal and allows the tri-axial ACC to acquire motion signals.

Figure 1:
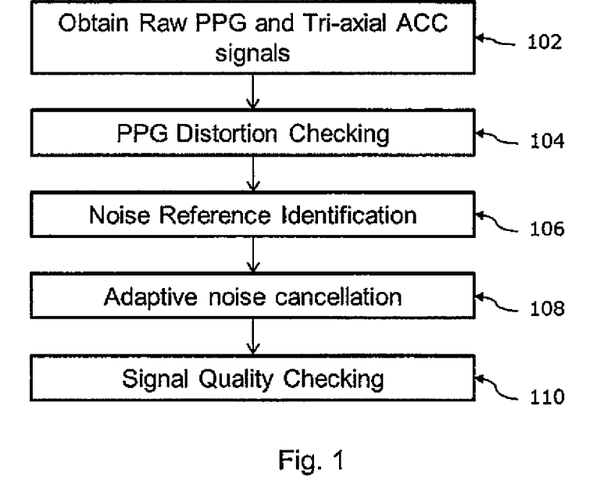
FIG. 1—Block diagram showing main steps according to example embodiments.

FIG. 1 shows a flow chart 100 illustrating a method of removing artifacts in physiological measurements according to example embodiments, comprising the steps of:

Obtaining raw PPG data and tri-axial ACC signals of a user, step 102;

Checking whether the PPG signal is distorted, step 104:

Identifying a noise reference from the tri-axial ACC signals, step 106;

Performing adaptive noise cancellation from the PPG signal with the identified ACC signal as noise reference, step 108;

Checking the signal quality of the filtered PPG signal, step 110.

Details of the method illustrated in FIG. 1 according to a first embodiment will now be described.

Checking Whether the PPG Signal is Distorted (Step 104)

Figure 2:
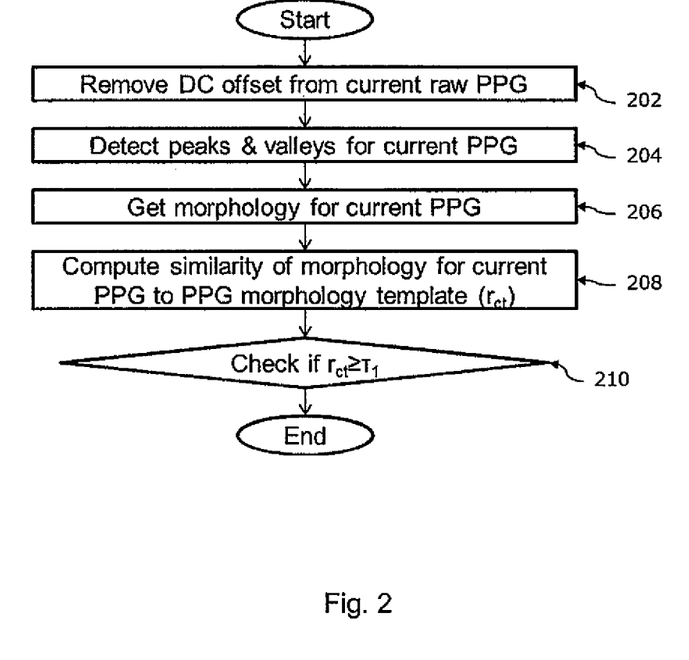
FIG. 2—Flowchart of PPG distortion checking by morphology method, according to a first embodiment.

The method of checking whether the PPG signal is distorted according to one embodiment is shown in the flowchart 200 in FIG. 2, and comprises:

Remove DC offset from current raw PPG signal, step 202;

Detect peaks and valleys for the current PPG signal, step 204;

Obtain morphology for the current PPG signal, step 206;

Compute similarity of morphology for the current PPG to PPG morphology template(s), step 208;

Determine signal distortion if the similarity is smaller than a predetermined threshold, step 210.

The template(s) can be obtained from either a previous measurement and can be updated in the current measurement or the template(s) can be obtained during a device initialization stage, for example when there is no stored template.

Identifying the Noise Reference (Step 106, FIG. 1)

Figure 3:
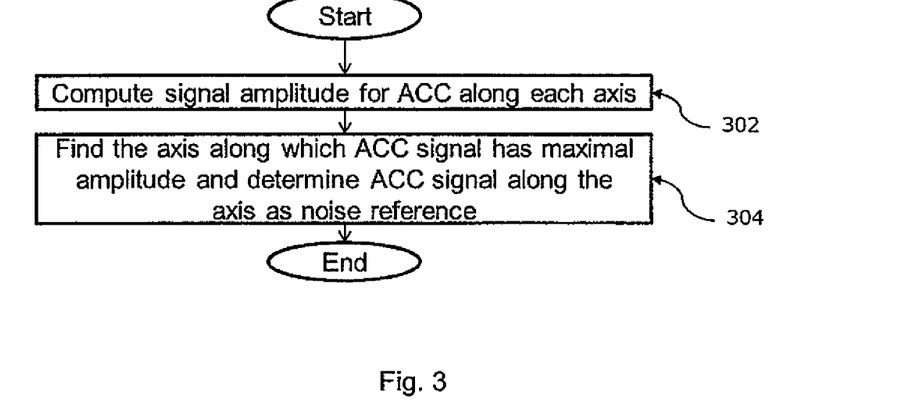
FIG. 3—Flowchart of noise reference identification by ACC signal amplitude in morphology method, according to the first embodiment.

The method of identifying the noise reference according to one embodiment is shown in the flowchart 300 in FIG. 3, and comprises:

Compute the signal amplitude for the ACC signal along each axis, step 302;

Find the axis along which ACC signal has the maximal amplitude and determine the ACC signal along that axis as noise reference, step 304.

Checking the Signal Quality of the Filtered PPG Signal (Step 110, FIG. 1)

Figure 4:
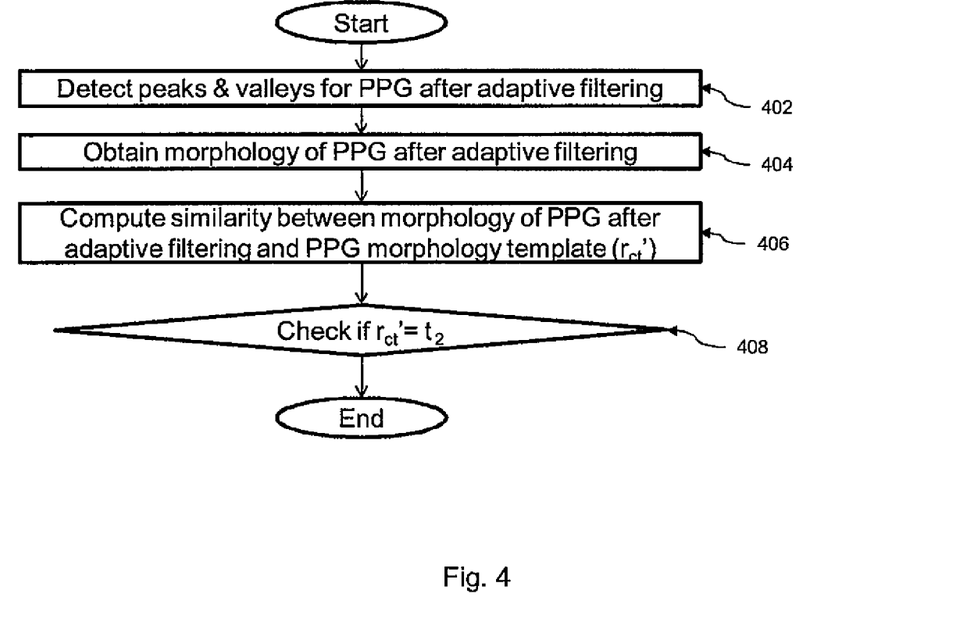
FIG. 4—Flowchart of signal quality checking according to example embodiments.

The method of checking the signal quality of the filtered PPG signal according to example embodiments is shown in the flowchart 400 in FIG. 4, and comprises:

Detect peaks and valleys for the filtered PPG signal, step 402;

Obtain morphology of the filtered PPG signal, step 404;

Compute similarity between the morphology of filtered PPG and PPG morphology template(s), step 406;

Accept the filtered PPG signal if the similarity is greater than a pre-determined threshold, step 408.

Figure 5:
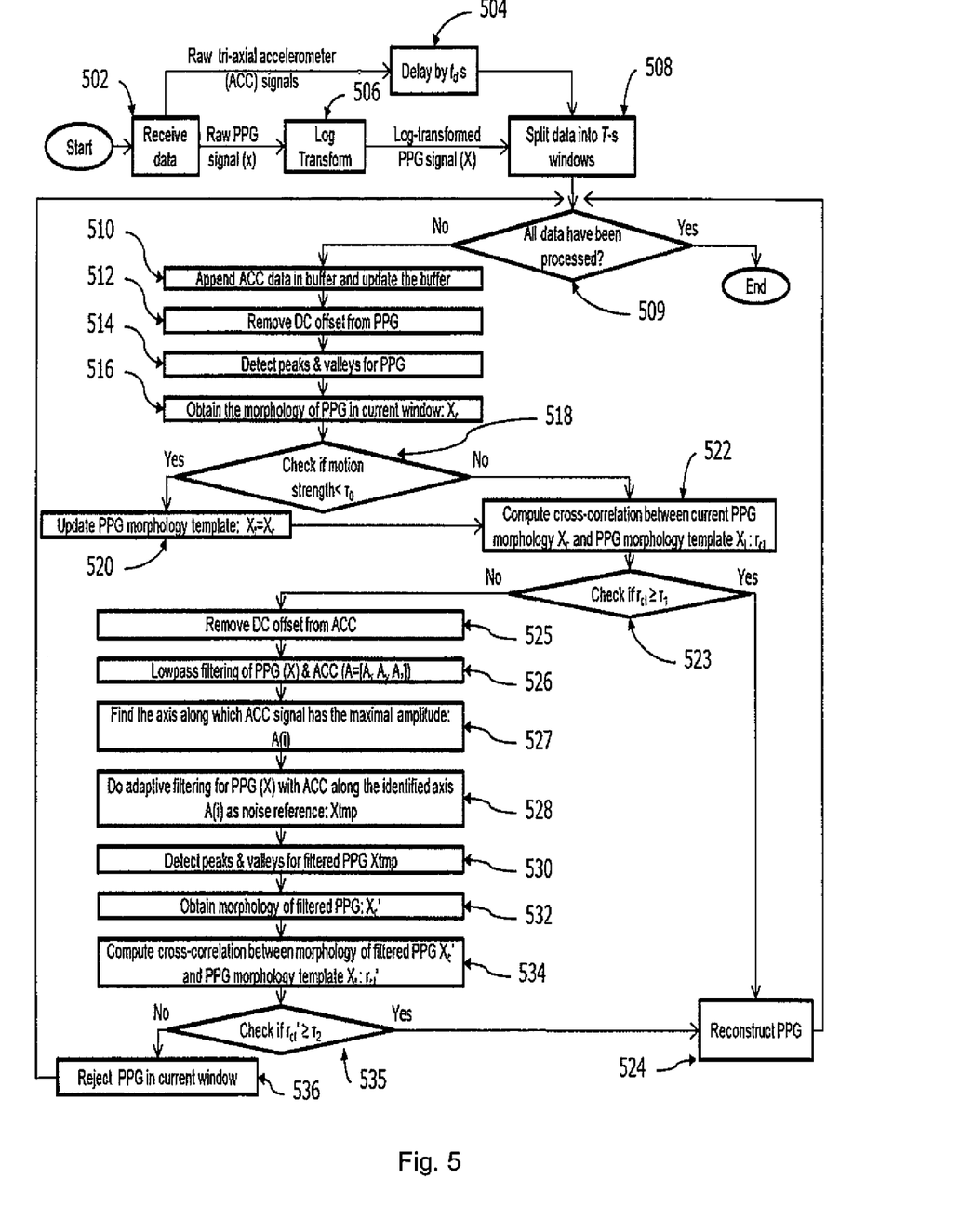
FIG. 5—Detailed process of artifact removal algorithm based on morphology method, according to the first embodiment.

FIG. 5 shows the complete process flow 500 of the first embodiment of the invention implemented into a wrist worn wearable device. The method comprises the steps of:

Obtaining raw PPG and accelerometer (ACC) signals of a user, step 502.

Applying a time delay of $t_d$ s to the ACC signals, step 504. The time delay preferably accounts for the delay in the occurrence of distortion in the measured PPG signal resulting from undergone motion, and may be in the range from about 100-130 ms.

Perform a log transform on the PPG signal, step 506.

Split the PPG and ACC data into a plurality of T-s (it can be either overlapping or non-overlapping windows) moving windows, preferably in the range from about 2 to 8-s, step 508;

In Each Processing Window

Determine whether all data has been processed, step 509, if no, append buffered ACC data to the beginning of ACC data in current window and update buffered ACC data, step 510. Specifically, if the adaptive filter has order of N, buffered ACC data have the length of N−1. Before updating, it is the last (N−1) samples of ACC signal along each axis in the previous window. After updating, it is the last (N−1) samples of ACC signal along each axis in the current window, which will be appended to the beginning of the ACC data in the next window and updated accordingly.

Remove DC offset from the PPG signal, preferably by subtracting the mean from the PPG signal, step 512.

Detect peaks and valleys of the PPG signal, step 514.

Figure 6:
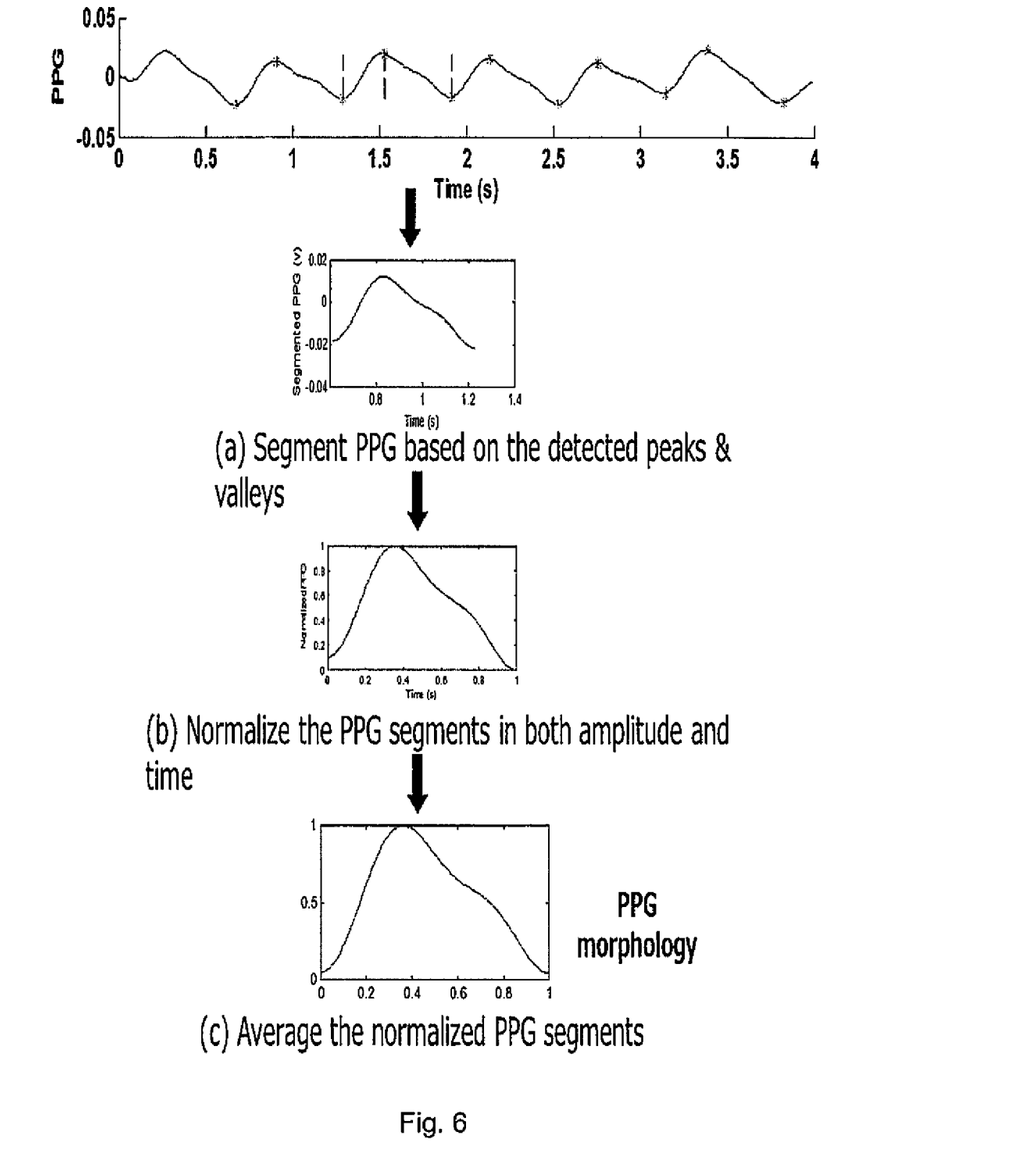
FIG. 6—Diagram for obtaining PPG morphology, according to example embodiments.

Obtain a current PPG morphology by segmenting the PPG (see FIG. 6a) based on the detected peaks and valleys, normalizing the PPG segments in both time and amplitude (see FIG. 6b), and averaging the normalized PPG segments (see FIG. 6c), step 516 in FIG. 5.

Check for motion strength, preferably by checking if along all 3 axes, the amplitude of the each and every ACC signal is less than a pre-determined threshold $\tau_0$, step 518. If yes, update the PPG morphology template, step 520. In the preferred embodiment, $\tau_0$ is pre-determined at about 0.15 g.

If no, compute the similarity, preferably the cross correlation, between the current PPG morphology and the PPG morphology template, step 522. If, at step 523, the similarity is not less than a pre-determined $\tau_1$, reconstruct the PPG for this window (step 524); otherwise, proceed to step 525. In the preferred embodiment, $\tau_1$ is pre-determined at about 0.85.

Remove DC offset from ACC signals, preferably by subtracting the mean from the ACC signal, step 525.

Perform lowpass filtering of the PPG and ACC signals, step 526.

Figure 7:
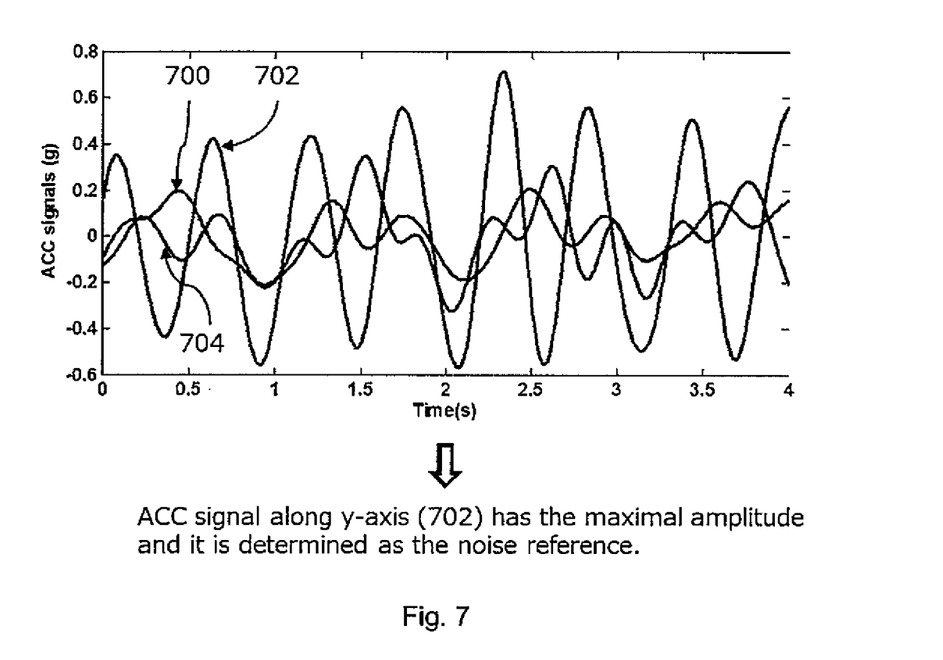
FIG. 7—Diagram on identification of the ACC signals correlate most with PPG distortion by signal amplitude, according to the first embodiment.

Identify the axis along which the ACC signal correlates most with the PPG distortion, in a preferred embodiment by identifying the axis with maximal amplitude, step 527. Example tri-axial lowpass filtered ACC data $A_x$ 700, $A_y$ 702, and $A_z$ 704 is shown in FIG. 7.

Perform adaptive filtering for the lowpass-filtered PPG signal with the lowpass-filtered ACC signal along the identified axis as the noise reference, step 528.

Detect peaks and valleys for the filtered PPG signal, step 530.

Obtain the morphology of the filtered PPG signal, step 532.

Compute the similarity, preferably the cross correlation, between the morphology of the filtered PPG signal and the PPG morphology template, step 534, for checking the reliability of the filtered PPG signal. If, at step 535, the similarity is not less than a pre-determined $\tau_2$, reconstruct the PPG signal for this window (step 524); otherwise, reject the PPG signal in the current window, step 536. In the preferred embodiment, $\tau_2$ is pre-determined at about 0.1.

Determine whether all data has been processed, step 509. If not, repeat the process (steps 510 to 536) for the next data window.

Figure 8:
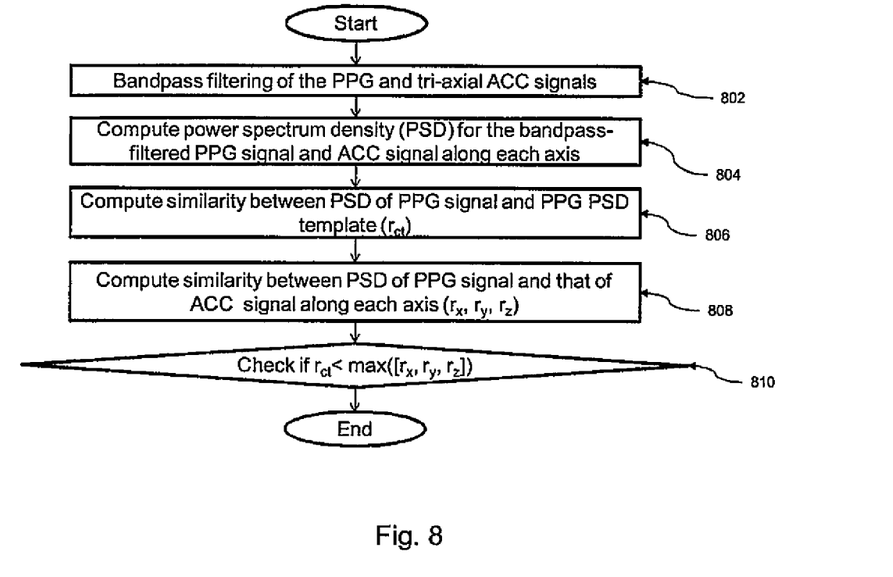
FIG. 8—Flowchart of PPG distortion checking by PSD method, according to the second embodiment.

FIG. 8 shows a flow chart 800 illustrating checking whether the PPG signal is distorted (step 104, FIG. 1) by a power spectrum density (PSD) method, according to a second embodiment, comprising:

Apply bandpass filtering to the PPG signal and each of the ACC signals, step 802.

Compute PSD for the PPG and each of the ACC signals, step 804.

Compute the similarity, preferably the cross correlation, between the PSD of the PPG signal and a PSD template of the PPG, step 806. The template(s) can be obtained from either a previous measurement and can be updated in the current measurement or the template(s) can be obtained during a device initialization stage, for example when there is no stored template.

Compute similarity between the PSD of the PPG signal and the PSD of the ACC signal along each axis, step 808.

Determine PPG distortion if the similarity between the PSD of the PPG signal and the PSD) template is smaller than the similarity between the PSD of the PPG signal and the PSD of the ACC signal along any axis, step 810.

Figure 9:
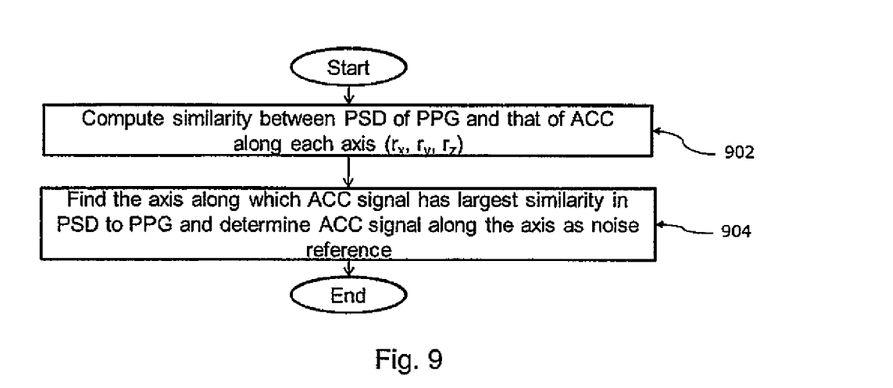
FIG. 9—Flowchart of noise reference identification by PSD method, according to the second embodiment.

FIG. 9 shows a flow chart 900 illustrating identifying the noise reference (step 106, FIG. 1) by the PSD method, according to the second embodiment, comprising:

Compute the similarity, preferably the cross-correlation, between the PSD of the PPG and the PSD of ACC along each axis, step 902.

Find the axis along which the ACC signal has the largest similarity in PSD) to the PPG and determine the ACC signal along that axis as the noise reference, step 904.

Figure 10:
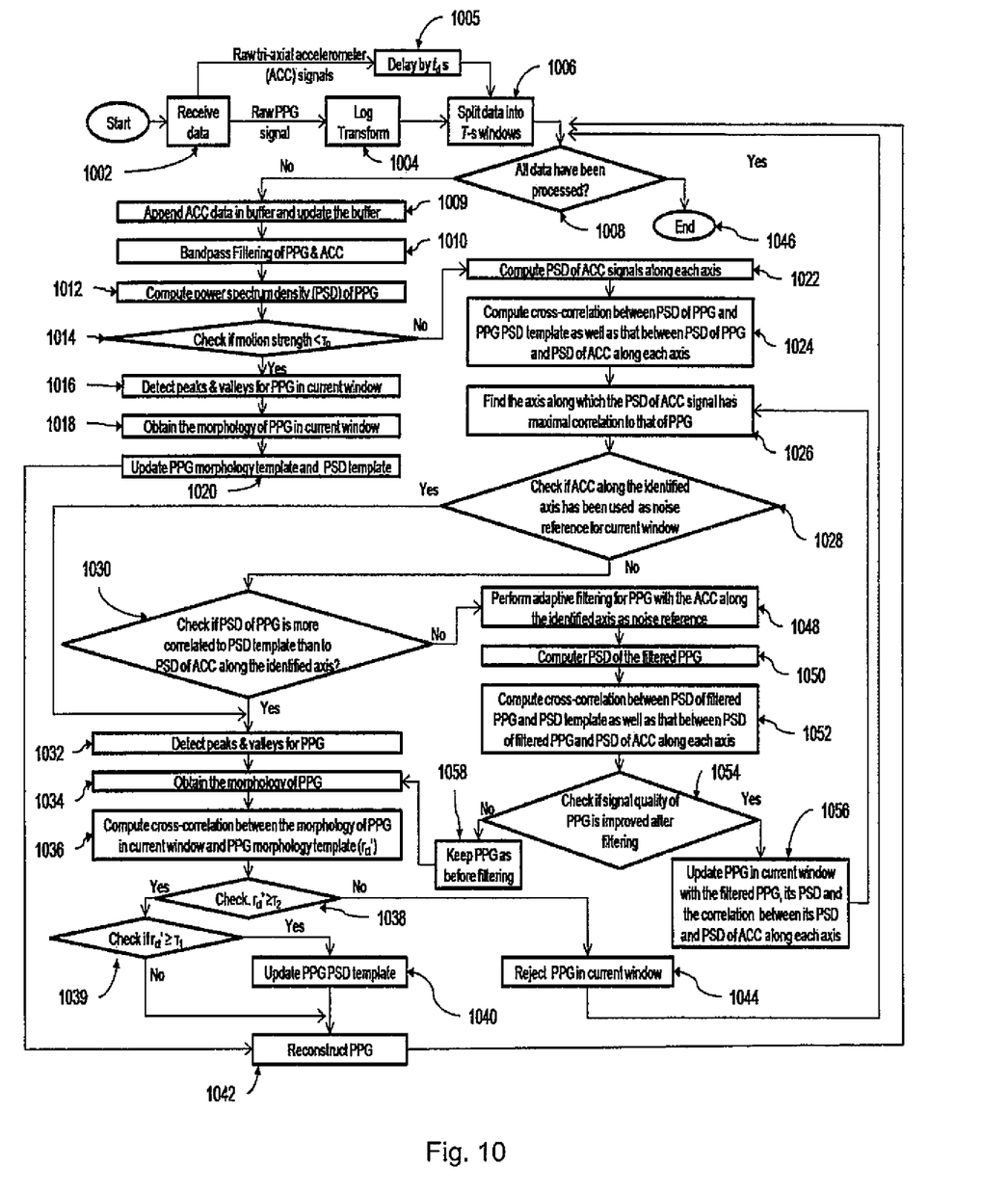
FIG. 10—Detailed process of artifact removal algorithm based on PSD method, according to the second embodiment.

FIG. 10 shows the complete process flow 1000 of the second embodiment of the invention, comprising:

Acquire raw PPG and ACC signals from the subject, step 1002.

Perform a log-transform on the PPG signal (step 1004), apply a time delay of $t_d$ s (step 1005) and split the PPG and ACC data into moving windows (it can be either overlapping or non-overlapping windows), at step 1006. The time delay preferably accounts for the delay in the occurrence of distortion in the measured PPG signal resulting from undergone motion, and may be in the range from about 100-130 ms In Each Processing Window, Determine whether all data has been processed, step 1008, if no, append buffered ACC data to the beginning of ACC data in current window and update buffered ACC data, step 1009. Specifically, if the adaptive filter has order of N, buffered ACC data have the length of N−1. Before updating, it is the last (N−1) samples of ACC signal along each axis in the previous window. After updating, it is the last (N−1) samples of ACC signal along each axis in the current window, which will be appended to the beginning of the ACC data in the next window and updated accordingly.

Apply bandpass filtering of the PPG and ACC signals, step 1010.

Compute the PSD of the PPG signal for the current window, step 1012.

Check for motion strength, preferably by checking if along all 3 axes, the amplitude of each and every ACC signal is less than a pre-determined threshold $\tau_0$, step 1014. In the preferred embodiment, $\tau_0$ is pre-determined at about 0.15 g. If yes, detect peaks and valleys for the bandpass filtered PPG signal, step 1016.

Obtain the morphology of the bandpass filtered PPG signal, step 1018, update the PPG morphology template and the PSD template, step 1020, reconstruct the PPG signal at step 1042, and return to step 1008.

If the answer at step 1014 (motion strength checking) is no, compute the PSD of the ACC signals along each axis for the current window, step 1022.

Compute the cross-correlation between the PSD of the PPG in the current window and the PPG PSD template, and the cross-correlation between the PSD of the PPG and the PSD of the ACC signals along each axis for the current window, at step 1024.

Identify the axis along which the PSD) of the ACC signal maximally correlates with that of the PPG signal, step 1026.

Check if the ACC signal along the identified axis has been used as a noise reference for the current window, step 1028.

If yes, proceed to step 1032. If no, check if the PSD of the PPG is more correlated to the PSD template than to the PSD of the ACC along the identified axis, step 1030.

If "Yes" at Step 1030:

Detect peaks and valleys for the PPG, step 1032, and obtain the morphology of the current PPG in the current window (as shown in FIG. 6 described above), step 1034.

Compute the cross-correlation between the morphology of the current PPG and the PPG morphology template, step 1036.

Check the cross-correlation between the morphology of the current PPG and the PPG morphology template, step 1038, for checking the reliability of the current PPG, which can be a filtered PPG (see steps 1048 to 1058 described below). If the correlation value is not less than a predetermined threshold, $\tau_2$, check if the correlation value is greater than a pre-determined threshold $\tau_1$ ($\tau_1 > \tau_2$), step 1039. If "yes", at step 1039, update the PPG PSD template (step 1040), reconstruct PPG (step 1042) and then loop back to step 1008. If "no", at step 1039, directly reconstruct PPG (step 1042) and then loop back to step 1008.

If "no" at step 1038, i.e, the correlation value is smaller than $\tau_2$, reject the PPG in current window, step 1044, and loop back to step 1008.

End the process if all data has been processed (steps 1008, 1046).

If "No" at Step 1030:

Perform adaptive filtering for the PPG signal with the identified ACC signal as noise reference, step 1048.

Compute the PSD of the filtered PPG signal, step 1050.

Compute the cross-correlation between the PSD of the filtered PPG signal and the PSD template as well as the cross-correlation between PSD of filtered PPG signal and that of the ACC signal along each axis, step 1052.

Check if the signal quality of the PPG is improved by adaptive filtering, i.e. check whether the correlation between the PSD of the PPG and the PSD template increases or whether the correlation between the PSD of the PPG and that of the noise reference decreases after adaptive filtering, step 1054.

If the signal quality is improved after adaptive filtering, update the PPG in the current window with the filtered PPG, update its PSD and the correlation between the PSD of the PPG and the PSD of the ACC along each axis, at step 1056, and return to step 1026. If the signal quality is not improved after the current adaptive filtering, keep the PPG as before the current filtering (indicated as step 1058), and go to step 1034.

Figure 11:
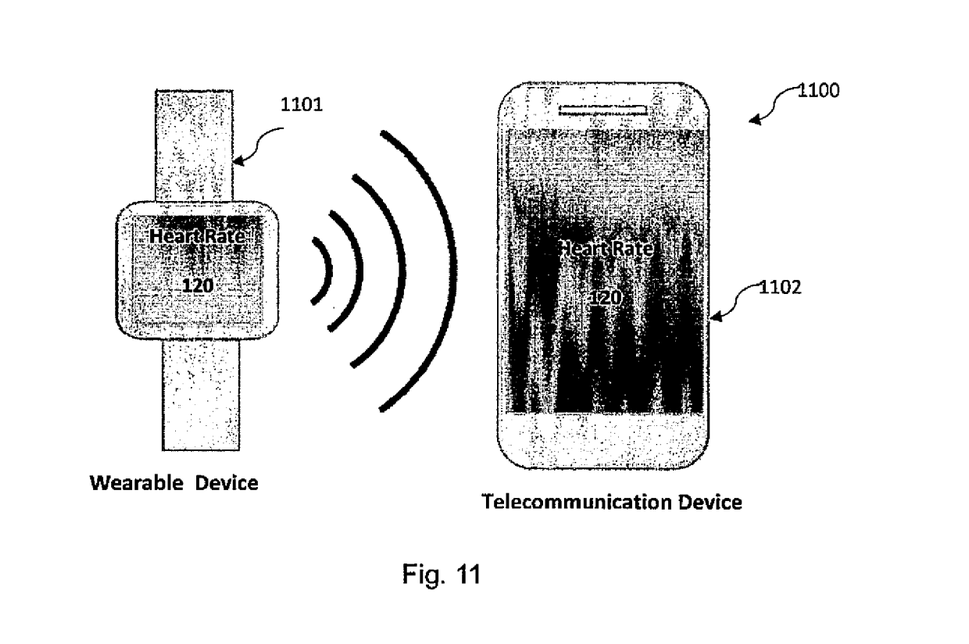
FIG. 11—Diagram of an assembly comprising a wearable device in the form of a wrist watch according to an example embodiment.

FIG. 11 shows an assembly 1100 comprising a wearable device in the form of a wrist watch 1101 according to an example embodiment. It will be appreciated that in different embodiments the device may also be in any other form suitable to be worn on any part of the user's body such as his/her arms, waist, hip or foot. The wrist watch 1101 obtains physiological measurements and motion data from a user, removes artifacts in the physiological measurements and communicates the result(s) wirelessly to a telecommunication device of the assembly 1100 such as a mobile phone 1102 or other portable electronic devices, or computing devices such as desk top computers, laptop computer, tab computers etc.

Figure 12:
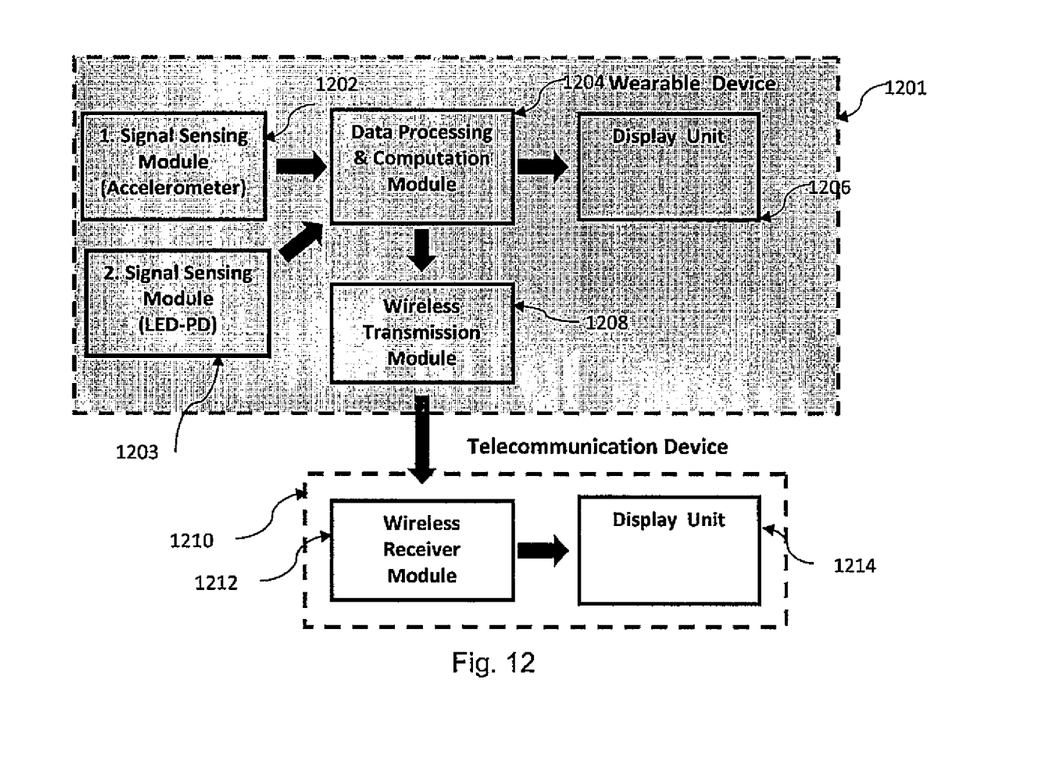
FIG. 12—Schematic block diagram of an assembly comprising a wearable device according to an example embodiment.

FIG. 12 shows a schematic block diagram of an assembly 1200 comprising a wearable device 1201 according to an example embodiment, for obtaining physiological measurements from a user and removing artifacts in the physiological measurements. The device 1201 includes a first signal sensing module 1202, such as an accelerometer or gyroscope, for obtaining the motion information of the user.

One non-limiting example of a preferred accelerometer that can be adapted for use in the device is a triple-axis accelerometer MMA8652FC available from Freescale Semiconductor, Inc. This accelerometer can provide the advantage of measuring acceleration in all three directions with a single package. Alternatively, several single-axis accelerometers oriented to provide three-axis sensing can be used in different embodiments.

Figure 13:
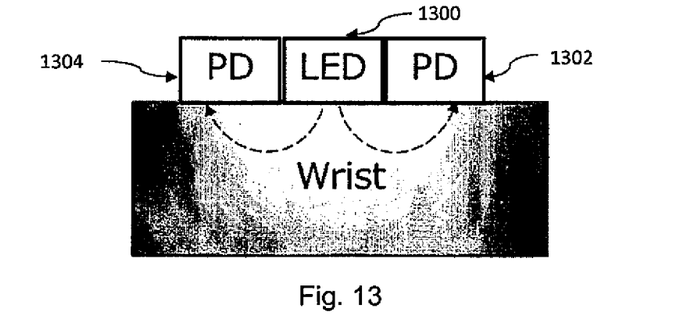
FIG. 13—Schematic illustration of a preferred LED-PD configuration for the measurement in reflectance mode for a wearable device of FIG. 11.

The device 1201 also includes a second sensing module 1203, such as an LED-PD module, for obtaining a physiological signal of the user. FIG. 13 shows a schematic illustration of preferred LED-PD configuration for the measurement in reflectance mode for a wearable device in the form of wrist watch 1101. The measurement is based on the amount of light by a LED 1300 reflected back to two PDs 1302, 1304.

One non-limiting example of a preferred LED-PD module that can be adapted for use in the device is composed of one LED, e.g. OneWhite Surface Mount PLCC-2 LED Indicator ASMT-UWB1-NX302, paired with one or multiple PDs, e.g. ambient light sensor TEMD5510FX01. Alternatively, the LED-PD module can be composed of multiple LEDs paired with one or multiple PDs.

The device 1201 also includes a data processing and computational module 1204, such as a processor, which is arranged to receive and process the acceleration information from the signal sensing module 1202 and the physiological signal from the measurement module 1203. The device 1201 also includes a display unit 1206 for displaying a result to a user of the device 1201. The device 1201 in this embodiment further includes a wireless transmission module 1208 arranged to communicate wirelessly with a telecommunications device 1210 of the assembly 1200. The telecommunication device 1210 includes a wireless receiver module 1212 for receiving signals from the wearable device 1201 and a display unit 1214 for displaying a result to a user of the telecommunication device 1210.

Figure 14:
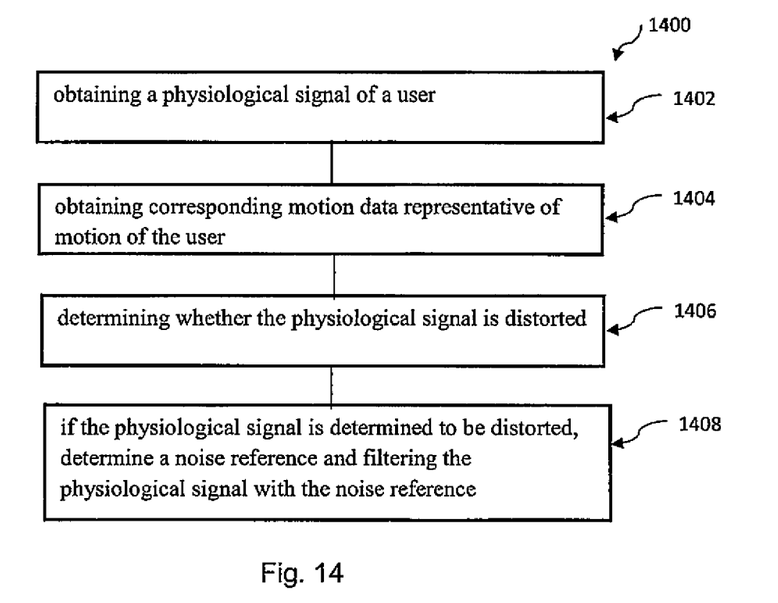
FIG. 14—Flowchart illustrating a method for removing artifacts in physiological measurements according to an example embodiment.

FIG. 14 shows a flowchart 1400 illustrating a method for removing artifacts in physiological measurements according to an example embodiment. At step 1402, a physiological signal of a user is obtained. At step 1404, corresponding motion data representative of motion of the user is obtained. At step 1406, it is determined whether the physiological signal is distorted. At step 1408, if the physiological signal is determined to be distorted, a noise reference is identified and the physiological signal is filtered with the noise reference.

Preferably, the method further comprises checking the reliability of the filtered physiological signal.

The obtained motion data may comprise tri-axial motion signals. Identifying the noise reference may comprise identifying the axis along which the motion signals has the maximal amplitude and using the motion signal along said axis as the noise reference. The method may comprise removing a DC offset from the motion signals prior to identifying the axis along which the motion signals has the maximal amplitude. The method may comprise lowpass filtering of the motion signals prior to identifying the axis along which the motion signals has the maximal amplitude.

Identifying the noise reference may comprise identifying the axis along which the motion signal has the maximal similarity in PSD to PPG signal and using the motion signal along said axis as the noise reference. The method may comprise bandpass filtering of the PPG and motion signals prior to identifying the axis along which the motion signal has the maximal similarity in PSD to PPG signal.

The determining whether the physiological signal is distorted may comprises comparing a similarity between a morphology of the physiological signal and a physiological morphology template. The similarity may comprise a cross-correlation between the morphology of the physiological signal and the physiological morphology template. The method may further comprise determining the morphology of the physiological signal by segmenting the physiological signal based on detected peaks and valleys; normalizing the physiological segments; and averaging the normalized physiological segments.

The determining whether the physiological signal is distorted may comprise computing the power spectrum density (PSD) of the physiological signal; computing the PSD of each of the motion signals; and determining whether a similarity between the PSD of the physiological signal and a PSD template is larger than a similarity of the PSD of the physiological signal and the respective PSDs of the motion signals. Determining whether a similarity between the PSD of the physiological signal and a PSD template is larger than a similarity of the PSD of the physiological signal and the respective PSDs of the motion signals may comprise identifying the axis along which the PSD of the corresponding motion signal has a maximal correlation with the PSD of the physiological signal; and determining whether the similarity between the PSD of the physiological signal and a PSD template is larger than a similarity of the PSD of the physiological signal and the PSD of the corresponding motion signal.

The method may further comprise, if the similarity between the PSD of the physiological signal and a PSD template is not larger than the similarity between the PSD of the physiological signal and the PSD of the corresponding motion signal performing filtering of the physiological signal with the corresponding motion signal as the noise reference; determining the PSD of the filtered physiological signal; and determining whether a signal quality of the physiological signal after the filtering is improved.

The method may further comprise, if the similarity between the PSD of the filtered physiological signal and a PSD template is not larger than the similarity between the PSD of the filtered physiological signal and the PSD of a motion signal along another axis, performing filtering of the filtered physiological signal with the motion signal along said other axis as the noise reference.

The physiological signal and the motion data may be are processed based on either non-overlapping or overlapping moving windows.

The physiological signal may comprise a PPG signal.

The motion data may comprise ACC data.

Figure 15:
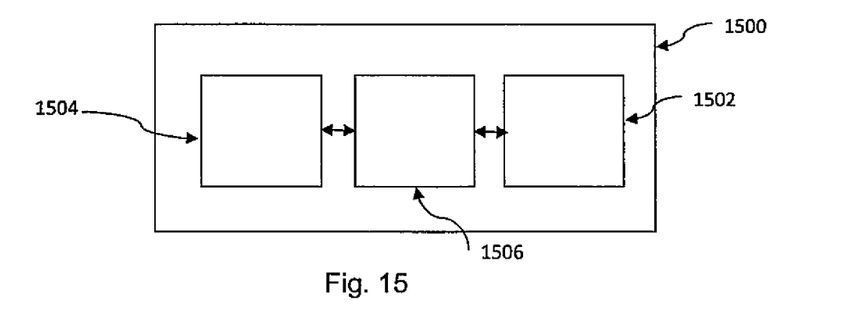
FIG. 15—Schematic drawing illustrating a device for removing artifacts in physiological measurements according to an example embodiment.

FIG. 15 shows a schematic drawings illustrating a device 1500 for removing artifacts in physiological measurements, according to an example embodiment. The device 1500 comprises a first sensor 1502 for obtaining a physiological signal of a user; a second sensor 1504 for obtaining corresponding motion data representative of motion of the user; and a processor 1506 configured for determining whether the physiological signal is distorted and, if the physiological signal is determined to be distorted, for identifying a noise reference and filtering the physiological signal with the noise reference.

Preferably, the processor is further configured for checking the reliability of the filtered physiological signal.

The obtained motion data may comprise tri-axial motion signals. Identifying the noise reference may comprise identifying the axis along which the motion signals has the maximal amplitude and using the motion signal along said axis as the noise reference. The processor 1506 may be configured for removing a DC offset from the motion signals prior to identifying the axis along which the motion signals has the maximal amplitude. The processor 1506 may be configured for lowpass filtering the motion signals prior to identifying the axis along which the motion signals has the maximal amplitude.

Identifying the noise reference may comprise identifying the axis along which the motion signal has the maximal similarity in PSD to PPG signal and using the motion signal along said axis as the noise reference. The method may comprise bandpass filtering of the PPG and motion signals prior to identifying the axis along which the motion signal has the maximal similarity in PSD to PPG signal.

The determining whether the physiological signal is distorted may comprise comparing a similarity between a morphology of the physiological signal and a physiological morphology template. The similarity may comprise a cross-correlation between the morphology of the physiological signal and the physiological morphology template. The processor 1506 may be configured for determining the morphology of the physiological signal by segmenting the physiological signal based on detected peaks and valleys; normalizing the physiological segments; and averaging the normalized physiological segments.

The determining whether the physiological signal is distorted may comprise computing the power spectrum density (PSD) of the physiological signal; computing the PSD of each of the motion signals; and determining whether a similarity between the PSD of the physiological signal and a PSD template is larger than a similarity of the PSD of the physiological signal and the respective PSD of the motion signals. Determining whether a similarity between the PSD of the physiological signal and a PSD template is larger than a similarity of the PSD of the physiological signal and the respective PSDs of the motion signals may comprise identifying the axis along which the PSD of the corresponding motion signal has a maximal correlation with the PSD of the physiological signal; and determining whether the similarity between the PSD of the physiological signal and a PSD template is larger than a similarity of the PSD of the physiological signal and the PSD of the corresponding motion signal.

The processor 1506 may be configured for, if the similarity between the PSD of the physiological signal and a PSD template is not larger than a similarity of the PSD of the physiological signal and the PSD of the corresponding motion signal performing filtering of the physiological signal with the corresponding motion signal as the noise reference; determining the PSD of the filtered physiological signal; and determining whether the signal quality of the physiological signal after the filtering is improved.

The processor 1506 may further be configured for, if the similarity between the PSD of the filtered physiological signal and a PSD template is not larger than the similarity between the PSD of the filtered physiological signal and the PSD of a motion signal along another axis, performing filtering of the filtered physiological signal with the motion signal along said other axis as the noise reference.

The processor 1506 may be is configured for processing the physiological signal and the motion data based on either non-overlapping or overlapping moving windows.

The physiological signal may comprise a PPG signal.

The motion data may comprise ACC data.

The device 1500 may be implemented in a wearable device.

The device 1500 may be implemented in an assembly comprising a wearable device and a communication device.

The device 1500 may be implemented in an assembly comprising a wearable device and a wireless communication device.

Embodiments of the present invention are advantageously capable of maximally removing motion artifacts in physiological measurements while being computationally inexpensive.

In the described embodiments, the cross-correlation may, for example, be calculated using the Pearson's correlation coefficient, r, as a measure of cross-correlation between two waveforms, x and y, which can be calculated as:

$$r = \frac{n\sum xy - (\sum x)(\sum y)}{\sqrt{n(\sum x^2) - (\sum x)^2} \sqrt{n(\sum y^2) - (\sum y)^2}} \quad \text{(Equation 1)}$$

It will be appreciated by a person skilled in the art that numerous variations and/or modifications may be made to the present invention as shown in the specific embodiments without departing from the spirit or scope of the invention as broadly described. The present embodiments are, therefore, to be considered in all respects to be illustrative and not restrictive. Also, the invention includes any combination of features, in particular any combination of features in the patent claims, even if the feature or combination of features is not explicitly specified in the patent claims or the present embodiments.

For example, while a wrist-worn device is described in some embodiments, the device may be worn on any part of the arms, hip, waist or foot of the user.

The invention claimed is:

1. A method for removing artifacts in physiological measurements, the method comprising the steps of:
    obtaining a physiological signal of a user;
    obtaining corresponding motion data representative of motion of the user;
    determining that the physiological signal is distorted by processing the physiological signal; and
    identifying a noise reference and filtering the physiological signal with the noise reference;
    wherein identifying the noise reference comprises identifying an axis along which the motion signal has a maximal amplitude and using the motion signal along said axis as the noise reference or identifying an axis along which the motion signal has a maximal similarity in PSD to the physiological signal and using the motion signal along said axis as the noise reference.

2. The method as claimed in claim 1, further comprising, after identifying the noise reference, checking a reliability of filtered physiological signal.

3. The method as claimed in claim 1, wherein identifying the axis along which the motion signal has the maximal amplitude comprises removing a DC offset from the motion signals.

4. The method as claimed in claim 1, wherein identifying the axis along which the motion signal has the maximal amplitude comprises lowpass filtering the motion signals.

5. The method as claimed in claim 1, wherein identifying the axis along which the motion signal has the maximal similarity in PSD to the physiological signal comprises bandpass filtering of the physiological and motion signals.

6. The method as claimed in claim 1, wherein determining whether the physiological signal is distorted comprises comparing a similarity between a morphology of the physiological signal and a physiological morphology template.

7. The method as claimed in claim 6, further comprising determining the morphology of the physiological signal by:
    segmenting the physiological signal based on detected peaks and valleys;
    normalizing the physiological segments; and
    averaging the normalized physiological segments.

8. The method as claimed in claim 1, wherein determining whether the physiological signal is distorted comprises:
    computing a power spectrum density (PSD) of the physiological signal;
    computing a PSD of each of the motion signals; and
    determining whether a similarity between the PSD of the physiological signal and a PSD template is larger than a similarity of the PSD of the physiological signal and the respective PSDs of the motion signals.

9. The method as claimed in claim 8, wherein determining whether the similarity between the PSD of the physiological signal and the PSD template is larger than the similarity of the PSD of the physiological signal and the respective PSDs of the motion signals comprises:
    identifying an axis along which the PSD of the corresponding motion data has a maximal correlation with the PSD of the physiological signal; and
    determining whether the similarity between the PSD of the physiological signal and the PSD template is larger than a similarity of the PSD of the physiological signal and the PSD of the corresponding motion data of the axis along which the PSD of the corresponding motion data has the maximal correlation with the PSD of the physiological signal.

10. The method as claimed in claim 9, comprising determining that the similarity between the PSD of the physiological signal and the PSD template is not larger than the similarity of the PSD of the physiological signal and the PSD of the corresponding motion data:
    performing filtering of the physiological signal with the corresponding motion data as the noise reference;
    determining a PSD of the filtered physiological signal; and
    determining whether a signal quality of the physiological signal after the filtering is improved.

11. A device for removing artifacts in physiological measurements, the device comprising:
    a first sensor for obtaining a physiological signal of a user;

a second sensor for obtaining corresponding motion data representative of motion of the user;

and a processor configured for determining that the physiological signal is distorted by processing the physiological signal and for identifying a noise reference and filtering the physiological signal with the noise reference;

wherein identifying the noise reference comprises identifying an axis along which the motion signals has a maximal amplitude and using the motion signal along said axis as the noise reference or identifying an axis along which the motion signal has a maximal similarity in PSD to the physiological signal and using the motion signal along said axis as the noise reference.

12. The device as claimed in claim 11, wherein the processor is further configured for, after identifying the noise reference, checking a reliability of filtered physiological signal.

13. The device as claimed in claim 11, wherein identifying the axis along which the motion signal has the maximal amplitude comprises removing a DC offset from the motion signals.

14. The device as claimed in claim 11, wherein identifying the axis along which the motion signal has the maximal amplitude comprises lowpass filtering the motion signals.

15. The device as claimed in claim 11, wherein identifying the axis along which the motion signal has the maximal similarity in PSD to the physiological signal comprises bandpass filtering of the physiological and motion signals.

16. The device as claimed in claim 11, wherein the determining whether the physiological signal is distorted comprises comparing a similarity between a morphology of the physiological signal and a physiological morphology template.

17. The device as claimed in claim 16, wherein the processor is configured for determining the morphology of the physiological signal by:
   segmenting the physiological signal based on detected peaks and valleys;
   normalizing the physiological segments; and
   averaging the normalized physiological segments.

18. The device as claimed in claim 11, wherein determining whether the physiological signal is distorted comprises:
   computing a power spectrum density (PSD) of the physiological signal;
   computing a PSD of each of the motion signals; and
   determining whether a similarity between the PSD of the physiological signal and a PSD template is larger than a similarity of the PSD of the physiological signal and the respective PSD of the motion signals.

19. The device as claimed in claim 18, wherein determining whether the similarity between the PSD of the physiological signal and the PSD template is larger than the similarity of the PSD of the physiological signal and the respective PSDs of the motion signals comprises:
   identifying an axis along which the PSD of the corresponding motion data has a maximal correlation with the PSD of the physiological signal; and
   determining whether the similarity between the PSD of the physiological signal and the PSD template is larger than a similarity of the PSD of the physiological signal and the PSD of the corresponding motion data of the axis along which the PSD of the corresponding motion data has the maximal correlation with the PSD of the physiological signal.

20. The device as claimed in claim 19, wherein the processor is configured for determining that the similarity between the PSD of the physiological signal and the PSD template is not larger than the similarity of the PSD of the physiological signal and the PSD of the corresponding motion data:
   performing filtering of the physiological signal with the corresponding motion data as the noise reference;
   determining a PSD of the filtered physiological signal; and
   determining whether a signal quality of the physiological signal after the filtering in improved.

21. The method as claimed in claim 9, comprising determining that a similarity between the PSD of the filtered physiological signal and the PSD template is not larger than the similarity between the PSD of the filtered physiological signal and a PSD of the corresponding motion data along a different axis, and performing filtering of the filtered physiological signal with the motion signal along the different axis as the noise reference.

22. The system as claimed in claim 18, wherein the processor is configured for determining that a similarity between the PSD of the filtered physiological signal and the PSD template is not larger than the similarity between the PSD of the filtered physiological signal and a PSD of the corresponding motion data along a different axis, and performing filtering of the filtered physiological signal with the motion signal along the different axis as the noise reference.

* * * * *